United States Patent [19]

Hickey et al.

[11] Patent Number: 5,338,752
[45] Date of Patent: Aug. 16, 1994

[54] SUBSTITUTED 2-IMIDAZOLONE DERIVATIVES, THEIR PREPARATION AND PHARMACEUTICAL COMPOSITIONS

[75] Inventors: Deirdre M. B. Hickey, Welwyn; David G. Cooper, Harlow; Albert A. Jaxa-Chamiec, Rickmansworth, all of England

[73] Assignee: SK&F Laboratories Ltd., Welwyn Garden City, England

[21] Appl. No.: 30,094

[22] PCT Filed: Sep. 10, 1991

[86] PCT No.: PCT/GB91/01543
§ 371 Date: May 10, 1993
§ 102(e) Date: May 10, 1993

[87] PCT Pub. No.: WO92/04331
PCT Pub. Date: Mar. 19, 1992

[30] Foreign Application Priority Data

Sep. 11, 1990 [GB] United Kingdom ............... 9019839.1

[51] Int. Cl.$^5$ .................. A61K 31/415; C07D 257/04; C07D 233/32; C07F 9/06
[52] U.S. Cl. ..................... 514/382; 514/392; 548/112; 548/252; 548/323.5
[58] Field of Search ..................... 548/323.5, 112, 252; 514/392, 382

[56] References Cited

PUBLICATIONS

CA 116(25):255613h Preparation of . . . Agonists, Hickey et al., p. 792, 1992.

Primary Examiner—Mary C. Lee
Assistant Examiner—Joseph K. McKane
Attorney, Agent, or Firm—Dara L. Dinner; Stephen Venetianer; Edward T. Lentz

[57] ABSTRACT

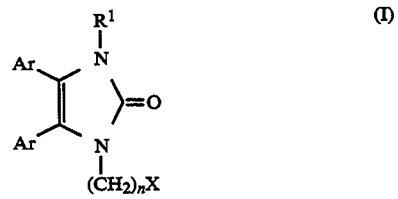

Substituted 4,5-diaryl-2-imidazolones of structure (I), in which each group AR is the same or different and is optionally substituted phenyl or optionally substituted heteroaryl; $R^1$ is hydrogen, alkyl, optionally substituted phenyl or optionally substituted heteroaryl; n is 4 to 12; and X is 5-tetrazolyl, $SO_3H$, $P(O)(OR)_2$, $P(O)(OH)_2$ or $P(O)(R)(OR)$ in which R is hydrogen acceptable salt thereof, processes for preparing them, pharmaceutical compositions containing them and their use in therapy, inter alia, in the treatment of cardiovascular disorders.

16 Claims, No Drawings

SUBSTITUTED 2-IMIDAZOLONE DERIVATIVES, THEIR PREPARATION AND PHARMACEUTICAL COMPOSITIONS

The present invention relates to novel substituted 2-imidazolone derivatives, processes for their preparation, pharmaceutical compositions containing them and their use in therapy.

The present invention therefore provides in a first aspect compounds of structure (I):

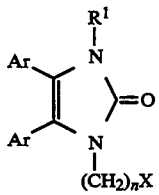

in which,
each group Ar is the same or different and is optionally substituted phenyl or optionally substituted heteroaryl;
$R^1$ is hydrogen, $C_{1-4}$alkyl, optionally substituted phenyl or optionally substituted heteroaryl;
n is 4 to 12; and
X is 5-tetrazolyl, $SO_3H$, $P(O)(OR)_2$, $P(O)(OH)_2$ or $P(O)(R)(OR)$ in which R is hydrogen or $C_{1-4}$alkyl, or a pharmaceutically acceptable salt thereof.

Suitably, each group Ar is the same and is optionally substituted phenyl or optionally substituted heteroaryl. More suitably, each group Ar is the same and is optionally substituted phenyl. Preferably each group Ar is the same and is unsubstituted phenyl.

Suitably, $R^1$ is hydrogen, $C_{1-4}$alkyl, optionally substituted phenyl or optionally substituted heteroaryl. Preferably $R^1$ is optionally substituted phenyl; most preferably unsubstituted phenyl.

Suitably, n is 4 to 12; preferably n is 4 to 8, most preferably n is 6 or 7.

Suitably, X is 5-tetrazolyl, $SO_3H$, $P(O)(OR)_2$, $P(O)(OH)_2$ or $P(O)(R)(OR)$ in which R is hydrogen or $C_{1-4}$alkyl. Preferably X is $SO_3H$.

Suitable substituents for phenyl groups Ar and $R^1$ include, for example, 1-3 groups which may be the same or different and are selected from $C_{1-4}$alkyl, halo$C_{1-4}$alkyl such as $CF_3$, halogen, hydroxy and $C_{1-4}$alkoxy.

Suitable heteroaryl groups include, for example, saturated or unsaturated 5- or 6-membered rings comprising 1 to 3 heteroatoms selected from nitrogen, oxygen and sulphur.

Preferred such rings include, for example, thienyl and furyl rings.

Particularly preferred compounds of structure (I) include:
sodium 7-(3,4,5-triphenyl-2-oxo-2,3-dihydroimidazol-1-yl)heptanesulphonate;
diethyl 7-(3,4,5-triphenyl-2-oxo-2,3-dihydroimidazol-1-yl)-heptanephosphonate;
7-(3,4,5-triphenyl-2-oxo-2,3-dihydroimidazol-1-yl)heptanephosphonic acid; and
ethyl 7-(3,4,5-triphenyl-2-oxo-2,3-dihydroimidazol-1-yl)methylphosphinate.

The compounds of structure (I) can be prepared using procedures analogous to those known in the art. The present invention therefore provides in a further aspect a process for the preparation of compounds of structure (I) in which X is other than 5-tetrazolyl which comprises reaction of a compound of structure (II):

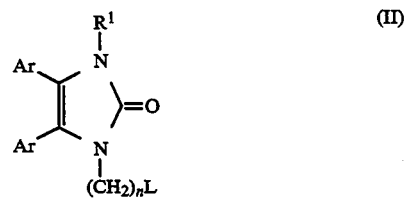

in which
Ar, $R^1$ and n are as described for structure (I) and L is a leaving group, with a suitable source of the group X; and optionally thereafter forming a pharmaceutically acceptable salt thereof. Compounds of structure (I) in which X is 5-tetrazolyl, can be prepared from compounds of structure (II) by standard techniques, for example, when L is bromine, by reaction with sodium cyanide in a suitable solvent such as dimethylsulphoxide, to form the intermediate compound in which L is cyano; followed by reaction with tri-n-butyl tin azide in, for example, tetrahydrofuran to form the desired compound of structure (I).

Suitable leaving groups L will be apparent to those skilled in the art and include, for example, halogen, such as bromine.

Suitable sources of the group X will again be apparent to those skilled in the art and include, for example, where X is $SO_3Na$, sodium sulphite.

The reaction between the compounds of structure (II) and the source of X is carried out in a solvent at elevated temperature. Preferably, for example where X is $SO_3Na$ the reaction is carried out in aqueous ethanol at reflux temperature for a suitable period to allow the reaction to go to completion; and where X is a phosphorus containing group the reaction is carried out in an organic solvent such as toluene or xylene.

The compounds of structure (II) can be prepared from compounds of structure (III):

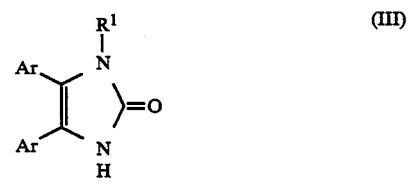

in which
Ar and $R^1$ are as described for structure (I) by reaction with, for example, a compound of formula $L^1(CH_2)_nL$, in which L and $L^1$ are suitable leaving groups, in the presence of a base such as potassium carbonate and a suitable solvent such as butanone. Suitable groups L are as described for structure (II). Suitable groups $L^1$ will be apparent to those skilled in the art, and include halogen, in particular bromine.

compounds of structure (III) are known or can be prepared by standard techniques.

The compounds of structure (I) and their pharmaceutically acceptable salts have been found to be $PGI_2$ agonists and as such are useful in therapy for the treatment of disease conditions in which such an effect is beneficial.

More specifically, the compounds are expected to have utility as antithrombotic, vasodilatory, antiatherosclerotic, antiinflammatory and cytoprotective agents. In particular, as antithrombotic and vasodilatory agents, the compounds are expected to be useful in the treatment of cardiovascular occlusive disorders including spasmodic and thrombotic disorders; coronary heart disease (primary and secondary prevention); stroke; post-operative thrombosis utilisation including post-angioplasty; deep vein thrombosis; peripheral vascular disease and Reynaud's disease. As antiatherosclerotic agents the compounds would be expected to reduce atherosclerotic plaque formation; and as cytoprotective agents the compounds would be expected to protect liver and gastric mucosa, protect against mucosal and ulcerative damage and reduce infarct size in myocardial infarct.

In addition to the foregoing utilities the compounds have antihyperlipidaemic properties and as such are expected to be of use as lipid lowering agents, and in the treatment of atherosclerosis and its sequelae.

In therapeutic use, the compounds of the present invention are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of structure (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the structure (I) or a pharmaceutically acceptable salt thereof calculated as the free base.

The present invention also provides a method of mimicking the effects of PGI$_2$ which comprises administering to a mammal in need thereof an effective amount of a compound of the structure (I) or a pharmaceutically acceptable salt thereof; and a method of treatment of cardiovascular disorders which comprises administering to a mammal in need thereof an effective amount of a compound of the structure (I) or a pharmaceutically acceptable salt thereof.

The pharmaceutically acceptable compounds of the invention will normally be administered to a subject in a daily dosage regimen. For an adult patient this may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the structure (I) or a pharmaceutically acceptable salt thereof calculated as the free base, the compound being administered 1 to 4 times per day. Suitably the compounds will be administered for a period of continuous therapy, for example for a week or more.

The following Examples serve to illustrate the invention. Temperatures are recorded in degrees centigrade.

EXAMPLE 1

Sodium 7(3,4,5-triphenyl-2-oxo-2,3-dihydroimidazol-1-yl)-heptanesulphonate

A mixture of 1,4,5-triphenylimidazol-2-one (15.3 g), dibromoheptane (50.6 g) and potassium carbonate (13.8 g) was heated at reflux temperature in dry butanone (750 ml) for 20 hours. The mixture was cooled, filtered and the filtrate evaporated to an oil which was chromatographed on silica gel (hexane/ethyl acetate) to give 1,4,5-triphenyl-3-(7-bromoheptyl)imidazole-2-one (11.1 g, 46%) as an oil.

NMR $\delta$ (CDCl$_3$) 1.2–1.9 (10H, m, 5×CH$_2$), 3.4 (2H, t, —CH$_2$Br), 3.7 (2H, t, —CH$_2$N), 6.8–7.4 (15H, m, 3×Ph) ppm.

A solution of 1,4,5-triphenyl-3-(7-bromoheptyl)-imidazol-2-one (2.0 g) in ethanol (10 ml) was refluxed with a solution of sodium sulphite (0.55 g) in water (5 ml) for 20 hours. More sodium sulphite (0.2 g) was added and refluxing continued for a further 20 hours. The mixture was evaporated to dryness, boiled in ethanol, filtered hot and evaporated to an oil. This was taken up in a small volume of ethanol, excess diethyl ether added and the precipitated solid filtered off and chromatographed on silica gel (dichloromethane/methanol 5:1). The resulting oil in methanol/water 1:1 was passed down an Amberlyst 15 ion exchange resin (Na form) and evaporated to a solid. This was taken up in ethanol and precipitated with diethyl ether giving sodium 7-(3,4,5-triphenyl-2-oxo-2,3-dihydroimidazol-1-yl)heptanesulphonate (0.49 g), 23%) as a white solid, m.p. 160° C.

Found: C, 63.47; H, 5.69; N, 5.04; S, 5.63% C$_{28}$H$_{29}$N$_2$NaO$_4$S+3.5% water Requires: C, 63.31; H, 5.89; N, 5.28; S, 6.04%

EXAMPLE 2

Diethyl 7-(3,4,5-triphenyl-2-oxo-2,3-dihydroimidazol-1-yl)heptanephosphonate A solution of 1,4,5-triphenyl-3-(7-bromoheptyl)-imidazol-2-one (1.0 g) and triethylphosphite (1.66 g) in xylene (5 ml) was heated at reflux temperature for 40 hours. The solution was evaporated to an oil and chromatographed on silica gel (ethyl acetate/ethanol)The resulting oil was taken up in diethyl ether, filtered and evaporated to give diethyl 7-(3,4,5-triphenyl-2-oxo-2,3-dihydroimidazol-1-yl)heptanephosphonate as a clear oil (0.84 g, 75%).

Found: C, 70.11; H, 7.37; N, 4.94% $C_{32}H_{39}N_2O_4P$
Requires: C, 70.31; H, 7.19; N, 5.12%

EXAMPLE 3

7-(3,4,5-Triphenyl-2-oxo-2,3-dihydroimidazol-1-yl)-heptanephosphonic acid

Diethyl 7-(3,4,5-triphenyl-2-oxo-2,3-dihydroimidazol-1-yl)heptanephosphonate (0.58 g) was dissolved in dry chloroform, cooled to −40° C. and to it was added trimethylsilyl iodide (1.05 g) over 2 mins under an atmosphere of nitrogen. The cooling bath was removed and the reaction mixture was stirred for 2.5 hours at room temperature then evaporated to an oil and re-evaporated from methanol, treated with excess aqueous sodium bicarbonate, evaporated to an oil and re-evaporated from methanol, water and ethanol respectively. The oil was taken up in ethanol, treated with excess aqueous sodium bicarbonate, evaporated to dryness then taken up in ethanol, filtered and the filtrate evaporated to an oil which solidified under ether. The solid was dissolved in water and passed down a Dowex 1×2–200 ion exchange resin in the formate form. Elution with aqueous formic acid gave on evaporation of the solvent 7-(3,4,5-triphenyl-2-oxo-2,3-dihydroimidazol-1-yl)heptanephosphonic acid (0.078 g, 15%) as a light brown foam.

Found: C, 66.50; H, 6.08; N, 5.39% $C_{28}H_{31}N_2O_4P$ +3% water
Requires: C, 66.50; H, 6.52; N, 5.54%

EXAMPLE 4

Ethyl 7-(3,4,5-triphenyl-2-oxo-2,3-dihydroimidazol-1-yl)methylphosphinate

A solution of 1,4,5-triphenyl-3-(7-bromoheptyl)-imidazol-2-one (2.0 g) and diethyl methylphosphinate (2.17 g) in toluene (15 ml) was heated at reflux temperature for 48 hours with the addition of more diethyl methylphosphonite (0.5 g) after 24 hours. Water (5 ml) was added and the solution was evaporated to an oil which was chromatographed on silica gel (ethyl acetate/ethanol). The resulting oil was taken up in diethyl ether, filtered and evaporated to give ethyl 7-(3,4,5-triphenyl-2-oxo-2,3-dihydroimidazol-1-yl)methylphosphinate (1.34 g, 65%) as a clear oil.

Found: C, 70.70; H, 7.53; N, 5.35% $C_{31}H_{37}N_2O_3P$ +0.9% $Et_2O$ +2% $H_2O$
Requires: C, 70.56; H, 7.36; N, 5.26%.

BIOLOGICAL DATA

METHOD FOR MEASUREMENT OF AGGREGATION OF WASHED HUMAN PLATELETS

Platelets were prepared from freshly drawn human blood. Blood was collected into acid citrate anticoagulant, centrifuged (5 min at 500 g), and the upper layer of platelet-rich plasma was removed. This platelet-rich plasma was incubated with aspirin (100 μM) for 10 min at 37° C. and then centrifuged (15 min at 200 g). The platelet pellet was resuspended (at approx. $1.5 \times 10^8$ cells/ml) in medium containing NaCl (145 mM), KCl (5 mM), $MgCl_2$ (1 mM), $CaCl_2$ (0.2 mM), Hepes (10 mM, ph 7.4 at 37° C.), glucose (10 mM), apyrase (10 μg/ml). Aggregation was monitored (as a change in optical density) at 37° C. in a 4 channel aggregometer (PAP-4 from Biodata Corp.). Fibrinogen (1 mg/ml) and $CaCl_2$ (1 mM) were added to aliquots of platelets that were continuously stirred. The test compound (or 0.1% DMSO vehicle) was added 2 min before the aggregatory stimulus (1 μM U46619). The extent of aggregation was assessed 4 min after addition of the stimulus, and was calculated as % of the control response in the absence of test compound. Dose-response curves were constructed for measurement of $IC_{50}$ values for each compound.

METHOD FOR MEASUREMENT OF $K_I$ FOR INHIBITION OF [$^3$H]ILOPROST BINDING TO HUMAN PLATELET MEMBRANES

Membranes were prepared from outdated platelet-rich plasma concentrates obtained from the Blood Transfusion Service. The platelets were homogenised in buffer containing Tris-Cl (5 mM, pH 7.4 at 20° C.) and EDTA (0.25 mM), and then centrifuged (10 min at 26,000 g). The membrane pellet was washed twice by homogenisation in buffer containing Tris-Cl (50 mM, pH 7.4 at 20° C.) and EDTA (0.25 mM), followed by centrifugation. For measurement of [$^3$H]iloprost binding, membranes (0.4–0.8 mg) were incubated in the presence of Tris-Cl (50 mM, pH 7.4 at 20° C.), $MgCl_2$ (4 mM), EDTA (40 μM), [$^3$H]iloprost (10 nM), DMSO (1.85%), and varying concentrations of the test compounds. For determination of non-specific binding, 20 μM iloprost was included. The tubes (triplicates for each condition) were set up on ice, and then incubated for 30 min at 37° C. The incubations were terminated by rapid filtration on Whatman GF/B filters using a Brandel Harvester. The filters were washed and then counted for radioactivity. The $K_i$ of the test compounds for inhibition of binding of [$^3$H]iloprost to human platelet membranes was calculated from the $IC_{50}$ for displacement of [$^3$H]iloprost binding.

RESULTS

| EXAMPLE NO. | AGGREGATION $IC_{50}$ (μM) | $K_i$ (μM) |
| --- | --- | --- |
| EXAMPLE 1 | 0.25 | 8 |
| EXAMPLE 2 | 5.50 | 30 |
| EXAMPLE 3 | 43 | 1.29 |
| EXAMPLE 4 | 21 | 19 |

We claim:
1. A compound of structure (I):

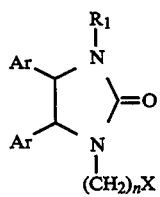

in which
  each group Ar is the same or different and is optionally substituted phenyl or optionally substituted heteroaryl, wherein the heteroaryl is independently selected from a saturated or unsaturated 5 or 6 membered ring comprising 1 to 3 heteroatoms selected from nitrogen, oxygen or sulfur,
  $R^1$ is hydrogen, $C_{1-4}$alkyl, optionally substituted phenyl or optionally substituted heteroaryl, wherein the heteroaryl is independently selected from a saturated or unsaturated 5 or 6 membered ring comprising 1 to 3 heteroatoms selected from nitrogen, oxygen or sulfur;
  n is 4 to 12; and
  X is 5-tetrazolyl, $SO_3H$, $P(O)(OR)_2$, $P(O)(OH)_2$, or $P(O)(R)(OR)$ in which R is hydrogen or $C_{1-4}$alkyl,
or a pharmaceutically acceptable salt thereof.

2. The compound according to claim 1 in which Ar and $R^1$ are optionally substituted phenyl.

3. A pharmaceutical composition comprising a compound according to claim 1 or a pharmaceutically acceptable salt thereof and a pharmaceutical carrier.

4. A method of treating cardiovascular disorders comprising administering an effective amount of a compound according to claim 1.

5. The compound according to claim 1 which is Sodium 7-(3,4,5-triphenyl-2-oxo)-2,3-dihydroimidazol-1-yl)heptane sulphonate.

6. The compound according to claim 1 which is Diethyl 7-(3,4,5-triphenyl-2-oxo-2,3-dihydroimidazol-1-yl)heptane phosphonate.

7. The compound according to claim 1 which is 7-(3,4,5-triphenyl-2-oxo)-2,3-dihydroimidazol-1-yl)heptane phosphonic acid.

8. The compound according to claim 1 which is Ethyl 7-(3,4,5-triphenyl-2-oxo-2,3-dihydroimidazol-1-yl)-methylphosphinate.

9. The compound according to claim wherein the heteroaryl is independently selected from thienyl or furyl.

10. The compound according to claim 2 wherein n is 4 to 8.

11. The compound according to claim 10 wherein n is 7.

12. The compound according to claim 2 wherein the phenyl is optionally substituted independently 1 to 3 times by $C_{1-4}$alkyl, halo $C_{1-4}$ alkyl, halogen, hydroxy or $C_{1-4}$alkoxy.

13. The compound according to claim wherein X is $SO_3H$.

14. A method of treating atherosclerosis, in a human in need thereof, which method comprises administering to said human an effective amount of a compound according to claim 1.

15. A method of treating thrombosis, in a human in need thereof, which method comprises administering to said human an effective amount of a compound according to claim 1.

16. A method of treating a human in need of vasodilation, which method comprises administering to said human an effective vasodilatory amount of a compound according to claim 1.

* * * * *